US008974403B2

(12) United States Patent
Yang et al.

(10) Patent No.: US 8,974,403 B2
(45) Date of Patent: Mar. 10, 2015

(54) APPARATUS FOR IDENTIFYING FALLS AND ACTIVITIES OF DAILY LIVING

(71) Applicant: National Chiao Tung University, Hsinchu (TW)

(72) Inventors: Bing-Shiang Yang, Hsinchu (TW); Chih-Chung Wang, Taichung County (TW); Sain-Ting Liao, Taichung (TW)

(73) Assignee: National Chiao Tung University (TW)

( * ) Notice: Subject to any disclaimer, the term of this patent is extended or adjusted under 35 U.S.C. 154(b) by 0 days.

(21) Appl. No.: 14/338,418

(22) Filed: Jul. 23, 2014

(65) Prior Publication Data

US 2014/0330173 A1    Nov. 6, 2014

Related U.S. Application Data

(62) Division of application No. 12/848,255, filed on Aug. 2, 2010, now abandoned.

(30) Foreign Application Priority Data

Apr. 21, 2010   (TW) .............................. 099112599 A

(51) Int. Cl.
*A61B 5/103* (2006.01)
*A61B 5/117* (2006.01)
*A61B 5/00* (2006.01)
*A61B 5/0488* (2006.01)
*A61B 5/11* (2006.01)

(52) U.S. Cl.
CPC .............. *A61B 5/7275* (2013.01); *A61B 5/0488* (2013.01); *A61B 5/1117* (2013.01); *A61B 5/0002* (2013.01); *A61B 5/1113* (2013.01); *A61B 5/746* (2013.01)
USPC ....................................... 600/595

(58) Field of Classification Search
CPC .. A61B 5/1113; A61B 5/1114; A61B 5/1116; A61B 5/1117
USPC ................................. 600/587–595
See application file for complete search history.

(56) References Cited

U.S. PATENT DOCUMENTS 7,532,977 B2 *   5/2009   Chen ............................. 701/433
2010/0049096 A1   2/2010   Ten Kate
2010/0324384 A1   12/2010   Moon et al.

FOREIGN PATENT DOCUMENTS

TW      I220003       8/2004
TW      200608938     3/2006
TW      200913959     4/2009

OTHER PUBLICATIONS

Taiwan Office Action in Application 099112599, filed Apr. 21, 2010.

*Primary Examiner* — Max Hindenburg
*Assistant Examiner* — Jonathan M Foreman
(74) *Attorney, Agent, or Firm* — Volpe and Koenig, P.C.

(57) ABSTRACT

The present invention provides and apparatus for distinguishing falls from activities of daily living (ADLs). First, the human movements and muscle activities would be obtained by an electromyography measuring unit and/or an inertia measuring unit to record ADLs, and falls would be distinguished from ADLs to trigger the protecting devices in time to prevent or decrease injury. In addition, the apparatus would be preset for different operational conditions to adapt different users by a setting unit to increase accuracy. Finally, the moving distance and the direction of the user would be obtained by the electromyography measuring unit and/or the inertia measuring unit to obtain the location thereof in an interior space.

3 Claims, 2 Drawing Sheets

APPARATUS FOR IDENTIFYING FALLS AND ACTIVITIES OF DAILY LIVING

CROSS REFERENCE TO RELATED APPLICATION

This application is a division of U.S. patent application Ser. No. 12/848,255, filed Aug. 2, 2010, which is incorporated by reference as if fully set forth.

FIELD OF INVENTION

The invention is related to a recognition device to distinguish the falls from activities of daily living (ADLs), more particularly to a recognition device measuring the physiological signals to distinguish the falls from ADLs.

BACKGROUND OF THE INVENTION

Falls are not a serious problem for adolescents and the adults. However, falls for the elderly may cause serious physical trauma and sequalae, such as degradation of mobility, the need for moving auxiliary equipment, etc. A further serious condition the elderly who fall may encounter is paralysis which can cause the elderly to be incapable of freely acting. Thus, the elderly who fall may need a caretaker to help their ADLs, which increase social costs. In addition to physical trauma, psychological sequalae may greatly impact the psychology of elderly who fall. In general, elderly who fall tend to reduce activities and avoid going outside so that they can reduce the risk of falls, which can result in a vicious circle for the elder.

Falls are the leading cause of unintentional deaths of the population over the age of 65 in the United States and many industrial countries. Because of the population growth and the population aging, the resources for medical care can not support the increasing demand for such care resulting from falls.

The current recognition technology for distinguishing the falls from activities of daily living (ADLs) is focused on recognizing after the events occur. For example, the fall warning and report are only generated to report the state after the faller's falling. The recognition technology can not provide an immediate protection. In addition, the recognition technology is mainly utilized to measure the physical parameter, such as acceleration and the angular velocity, by the inertia sensor, or utilized to recognize based on the posture of the users and the lasting period of the posture. However, this technology can not distinguish the passive actions from the active actions and can not accurately recognize the fall state, such as the stumble or the slip.

Moreover, some recognition technology is utilized to capture images of the user by image capturing devices so as to compare the captured images with the pre-stored data of falls. However, the greatest disadvantage of such technology is that the utility and effectiveness of conventional systems depends on the position where the image capture devices are installed. In fact, each of the image capture devices can only capture the image within a specific domain. Recognition technology can be improved for, for example, a blind corner, where the image of a user is hindered visually and can not be captured, by increasing the numbers of the image capture devices to make the blind spot area included within the capturing domain. However, there is still a problem which is difficult to overcome for using such devices in outdoor space.

Therefore, to overcome the drawbacks from the prior art and to meet the present needs, the Applicant dedicated in considerable experimentation and research, and finally accomplished the "Apparatus for Identifying Falls and Activities of Daily Living" of the present invention to provide a portable recognition device. In addition to inertia sensors, it is utilized to sense physiological signals by the physiological sensor for measuring the voluntary action and the reflex action, which can recognize the rebalancing action generated because of the falls to improve the recognition rate. The present invention is briefly described as follows.

SUMMARY OF THE INVENTION

To solve the above drawbacks, the present invention provides a portable fall recognition device for increasing the recognition rate and providing an immediate protection for the fallers so the device is utilized to measure the physiological signals to distinguish the falls from ADLs quickly and to be triggered to achieve a protecting effect when the fall happens.

According to the first aspect of the present invention, a recognition device is provided. The recognition device includes a physiological sensor unit measuring a physiological signal; and a recognition unit determining whether a fall is going to happen through processing the physiological signals.

Preferably, the recognition device further includes an inertia sensor unit obtaining motion signals provided to the recognition unit for determining whether the fall is going to happen; and a computing unit computing the physiological signals and the motion signals to obtain a computed result.

Preferably, the recognition unit receives the computed result to determine whether the fall is going to happen.

Preferably, the inertia sensor unit is at least one of an accelerometer and a gyroscope.

Preferably, the recognition device further includes a memory unit storing the computed result and a signal threshold; and an output unit outputting the computed result and a determining result generated by the recognition unit.

Preferably, the signal threshold is generated by the computing unit based on the stored computing result.

Preferably, the recognition device further includes a setting unit setting at least one of the physiological signal and the motion signal to be an exception signal representing a specific motion, wherein the specific motion represents a normal action for a specific controlled user but represents a comparable fall for a normal person.

Preferably, the signal threshold is one of respective signal thresholds of the physiological and the motion signals, and the recognition unit determines that the fall happens when at least one of the physiological signal and the motion signal is higher than the respective signal threshold and different from the exception signal.

Preferably, the recognition device further includes a positioning unit obtaining a location of a specific controlled user in a space via processing an arrangement of the space and a distance having been moved and a moving direction of the specific controlled user in the space; and a warning unit providing an information corresponding to the fall of the specific controlled user in the space, wherein the output unit transmits the information to an institution for generating a medical suggestion, and the computing unit computes the physiological signal and the motion signal to obtain the distance having been moved and the moving direction.

Preferably, the information includes a predictable injury corresponding to the location when the fall happens.

Preferably, the recognition device further includes a protecting device being triggered to achieve a protecting effect when the fall happens.

Preferably, the physiological sensor unit is an electromyography sensor unit.

Preferably, the physiological sensor unit further includes a health sensor unit, wherein the health sensor is at least one of a clinical thermometer, a sphygmomanometer, a glucometer, a pedometer, an oximeter, an electrocardiography and an electroencephalography.

According to the second aspect of the present invention, a fall positioning device is provided. The fall positioning device includes a sensor unit obtaining an sensor signal; a recognition unit processing the sensor signal to determine whether a fall is going to happen; and a positioning unit obtaining a location of a controlled user in a space via processing an arrangement of the space and a distance having been moved and a moving direction of the controlled user in the space.

Preferably, the fall positioning device further includes a computing unit computing the sensor signal to obtain the distance having been moved and the moving direction and provide a computed result to the recognition unit for determining whether the fall is going to happen; a warning unit providing an information corresponding to the fall of the controlled user in the space; and an output unit transmitting the information to an institution to render a medical suggestion.

Preferably, the information includes a predicted injury corresponding to the location when the fall happens, and the arrangement is a compartment configuration and furnishings of an interior space.

Preferably, the sensor unit is a physiological sensor unit.

According to the third aspect of the present invention, a fall recognition device is provided. The fall recognition device includes a setting unit setting a specific signal indicative of a specific motion to be an exception signal representing the specific motion of a specific controlled user, wherein the specific motion represents a normal action of the specific controlled user but represents the fall of a normal person; and a recognition unit determining whether a fall is going to happen by taking the exception signal into consideration.

Preferably, the fall recognition device further includes a sensor unit obtaining a sensor signal; and a computing unit computing the sensor signal and providing a result for the recognition unit to compare with the exception signal so as to determine whether the fall is going to happen.

Preferably, the fall is regarded as happening by the recognition unit when the sensor signal is different from the exception signal and is higher than a signal threshold.

Preferably, the signal threshold is a fall reference signal generated based on activities of daily living of the specific controlled user.

The present invention is capable to improve the recognition rate and protect the user from injury and can accordingly overcome the drawbacks in the prior art. The above aspects and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

Figure 1:
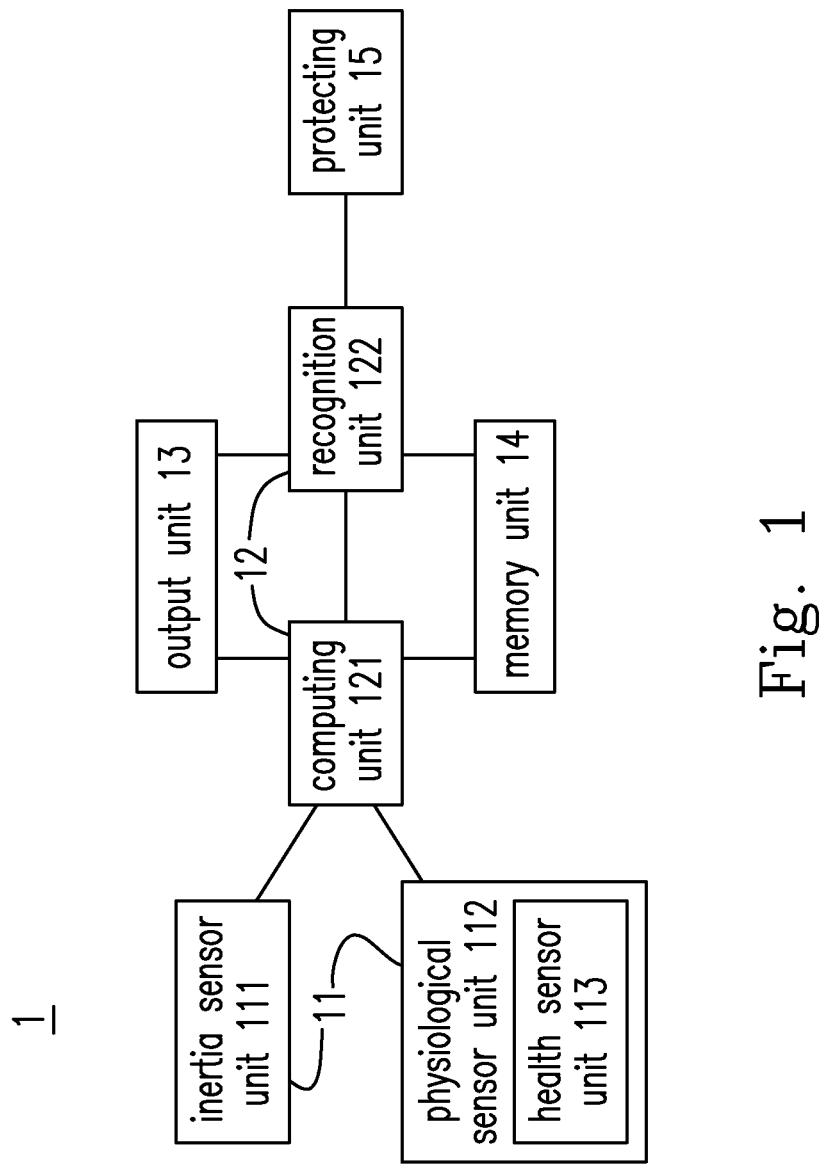
FIG. 1 is a block diagram schematically illustrating the first embodiment of the recognition device according to the present invention.

The present invention will now be described more specifically by the following embodiments. However, it is to be noted that the following descriptions of preferred embodiments of this invention are presented herein for the purposes of illustration and description only; it is not intended to be exhaustive or to be limited to the precise form disclosed.

In general, a voluntary action is an action generated by muscle contraction that is stimulated by a myoelectric signal which is generated from the brain via the nervous system. However, reflex action is not stimulated via the brain, and a myoelectric signal for the reflex action is generated more quickly than the myoelectric signal for the voluntary action. When the human body is about to lose balance in an unpredictable condition, the human body will generate a rebalancing action through at least one of the reflex action and the voluntary compensatory movement. Thus, the present invention provides a device to determine fall action by the myoelectric signal generated from the action mechanism.

In order to analyze the myoelectric signal during falling, the electromyography sensor device can be configured on the muscle group that is usually used for the rebalancing action when the fall happens, such as the deltoid, the trapezius, the tibialis anterior and the gastrocnemius lateralis of the limbs. Since the respective activation states of the muscle groups are different from each other, the respective maximal voluntary contraction (MVC) of the muscle groups should be measured in advance in order to normalize the respective activation states of the muscle groups for analyzing and comparing with each other.

The present invention provides an embodiment that an electromyography sensor is used for measuring ADLs, falls and the difference therebetween. Table 1 shows the MVCs of the ADLs and the falls as follows. The ADLs and the falls can be distinguished definitely through the peak value of the myoelectric signal generated from the aforementioned muscle groups. In addition, there is some data which is more than normalized data in Table 1. It might be because a lot of myoelectric signals are generated in order to quickly activate the muscle groups for reflex actions. Thus, it would not influence the relative result and the comparison between the normalization of the MVC and the activation states of the muscle groups.

TABLE 1

| | | signal | |
| --- | --- | --- | --- |
| muscle | | ADLs (% MVC) | Falls (% MVC) |
| deltoid | right | 15.79 | 78.55 |
| | left | 9.57 | 68.50 |
| trapezius | right | 27.96 | 87.96 |
| | left | 18.82 | 68.39 |
| tibialis anterior | right | 41.53 | 109.63 |
| | left | 43.38 | 127.41 |
| gastrocnemius lateralis | right | 45.65 | 148.15 |
| | left | 39.52 | 157.70 |

In addition, the present invention provides another embodiment that an electromyography sensor and an inertia sensor can also be used for identifying falls. Table 2 shows fall response rate and the average recognition time of the electromyography sensor and the inertia sensor as follows. If there is enough time for identifying, the fall recognition rates of the electromyography sensor and the inertia sensor is high enough to distinguish falls from ADLs. However, the fall recognition device would not be a device with high practicability if it is only improved to increase the fall recognition rate and to decrease the error rate. If the fall recognition device can be improved to keep a high accuracy rate and decrease the recognition time at the same time, there is enough time to trigger the additional protecting device immediately to achieve a protecting effect when the fall happens. According to the data in Table 2, both of the response rate and the recognition time of the myoelectric signal are better than those of the inertia signal so that the present invention provides a fall recognition device using the physiological sensor to measure the myoelectric signal for distinguishing falls from ADLs.

TABLE 2

| | Response rate | | | Average recognition time |
|---|---|---|---|---|
| | 100 ms | 300 ms | 500 ms | |
| myoelectric signal | 53.4% | 81.2% | 90% | 161 ms |
| inertia signal | 6% | 61% | 90% | 282 ms |

FIG. 1 is a block diagram illustrating the first embodiment of the recognition device 1 in the present invention. The recognition device 1 includes an inertia sensor unit 111, a physiological sensor unit 112, a computing unit 121, a recognition unit 122, an output unit 13, a memory unit 14 and a protecting unit 15.

Preferably, the physiological sensor unit 112 can be an electromyography sensor unit, which can measure the physiological reactions of the muscle groups, such as myoelectric signals, to obtain the physiological signal for determining whether the fall is going to happen. In addition, since the physiological sensor unit 112 should keep sensing for distinguishing falls from the ADLs when a fall happens, the physiological sensor unit 112 would measure continuously the signal of the ADLs to obtain the information of the ADLs, which can record the health state and the amount of exercise. Moreover, the recognition device 1 can generate a signal threshold based on the information of the ADLs. If the physiological signal measured by the recognition device 1 exceeds the signal threshold, the recognition device 1 can determine that a fall is going to happen.

Preferably, the inertia sensor unit 111 can be an accelerometer and/or a gyroscope, wherein the variance of the acceleration or the angular velocity of the user can be measured respectively thereby. The recognition device 1 can determine whether the fall is going to happen or not by a motion signal generated by the acceleration and the angular velocity. Since the recognition device 1 would determine the fall when the fall is going to happen, the inertia sensor unit 111 should measure continuously so that the motion signal of the ADLs can be generated. Thus, a signal threshold can be generated based the motion signal of the ADLs for determining whether the fall is going to happen. In addition, the inertia sensor unit 111 can also be a ADLs recorder to record the ADLs of the user.

In the aforementioned embodiment, the computing unit 121 can compute to obtain the motion information of the user. For example, the computing unit 121 can compute to estimate a distance having been moved and the moving direction of the user to recognize the motion information of the user. The computing unit 121 can compute the physiological signal and the motion signal generated respectively by the physiological sensor unit 112 and the inertia sensor unit 111 for forming a computed result to recognize the motion information of the user. In addition, the memory unit 14 can store the computed result to record the acting pattern of the user in daily life and the computing unit 121 can further generate a signal threshold through the computing result, wherein the signal threshold also can be stored in the memory unit 14. The signal threshold can be a specific signal level which is higher than the signal measured from the ADLs of the user. Thus, the motion would be determined as the fall if the physiological signal or the motion signal is higher than the signal threshold.

In the aforementioned embodiment, the physiological sensor unit 112 and the inertia sensor unit 111 can be called together as a sensor unit 11, and the recognition unit 122 can determine whether the fall is going to happen based on the computed result computed from the physiological signal and the motion signal generated by the sensor unit 11. In addition, the recognition unit 122 determines whether the fall is going to happen according the signal threshold.

Preferably, when the signals measured by the inertia sensor unit 111 and/or the physiological sensor unit 112 is higher than the signal threshold, the recognition unit 122 can determine the fall is going to happen. In addition, the physiological sensor unit 112 can be configured on the eight muscle groups described previously, some of the eight muscle groups or other muscle groups. Preferably, if some of the signals measured from the sensors configured on different muscle groups are higher than the signal threshold, it can be regarded that the physiological signal of the physiological sensor unit 112 is higher than the signal threshold. For example, if the signals measured by more than three of the eight physiological sensor unit are higher than the signal threshold, it can be regarded that the fall is going to happen.

In the aforementioned embodiment, the output unit 13 can output the computed result to provide the data about the ADLs of the user, for example, the activity data during wearing the recognition device and the state during sports. In addition, the output unit 13 can output the determining result to provide the medical institution so that the medical worker can reach the scene immediately to perform the first aid.

In the aforementioned embodiment, the protecting unit 15 can be a protecting airbag device. When the fall occurs, the protecting unit is triggered to achieve a protecting effect. In general, when a fall happens, the user would have some injuries at certain parts of the body, for example, the hand, the hip joint, the head, etc., wherein the hand might fracture because the user tries to support himself by hands, and the hip joint might fracture because the user falls backwards or laterally. Preferably, the protecting unit 15 can be configured to prevent the aforementioned injury. For example, the protecting unit can be configured on the hip to prevent the fracture of the hip joint, on the hand to prevent the fracture of the hand, and on the head to prevent bruises. However, the recognition device 1 might not be configured on the aforementioned part of the body so the protecting unit 15 can be connected with the recognition device 1 by wires or over a wireless network.

Preferably, the computing unit 121 and the recognition unit 122 can be combined as a computing recognition unit 12 to perform computing and recognizing at the same time.

Preferably, the recognition device 1 is a portable device, which can be tied around the waist to detect all the time.

In the aforementioned embodiment, the physiological sensor unit 112 can also include a health sensor unit 113. The health sensor unit 113 can be at least one of a clinical thermometer, a sphygmomanometer, a glucometer, a pedometer, an oximeter, an electrocardiography, an electroencephalography, etc. to record the health state of the user. When an unusual signal is generated by the motion of the user, the output unit 13 can output the signal to the medical institute. In addition, the physiological signal also can be the information to manage the health.

Figure 2:
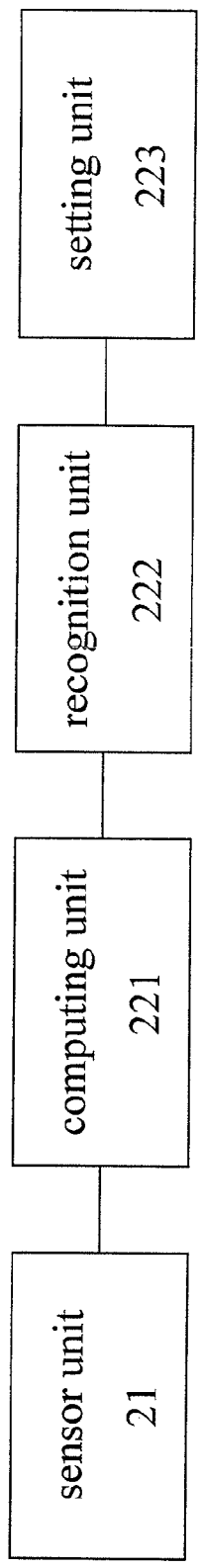
FIG. 2 is a block diagram schematically illustrating the second embodiment of the fall recognition device according to the present invention.

FIG. 2 is a block diagram illustrating the second embodiment of the fall recognition device 2 in the present invention. The fall recognition device 2 includes a sensor unit 21, a computing unit 221, a recognition unit 222 and a setting unit 223.

In the aforementioned embodiment, the sensor unit 21 is configured to measure a sensor signal and the computing unit 221 is configured to compute the sensor signal. The computed result can be stored in the computing unit 221 or a memory unit. In addition, a signal threshold, which is a fall reference to determine whether the fall is going to happen, can be generated from the computed result computed based on the sensor signals measured continuously through the ADLs. Generally, the recognition unit 222 would determine the fall is going to happen if the sensor signal is higher than the signal threshold, and the recognition unit 222 would determine the fall does not happen if the sensor signal is lower than the signal threshold.

In fact, every user has their respective habits. Although some signals corresponding to the habits might be higher than the signal threshold, the habits are common actions for the specific user. For example, if the specific user does some dangerous works, the specific physiological signals corresponding to the dangerous works might be always higher than the signal threshold so that the recognition device 2 would always generate the wrong result. Thus, the specific physiological signals corresponding to the dangerous works can be pre-measured by the sensor unit 21 and preset to be an exception signal by the setting unit 223.

In the aforementioned embodiment, the exception signal represents the specific motion of the specific user and the specific motion represents a normal action for the specific user. However, the exception signal represents the fall of the normal user. Thus, the exception signal needs to be preset in the fall recognition device 2 to adjust for the different users.

In the aforementioned embodiment, when the recognition unit 222 determines whether the fall is going to happen, the recognition unit 222 must take the exception signal into consideration to compare the sensor signal with the exception signal if the sensor signal measured by the sensor unit 21 is higher than the signal threshold. Therefore, after comparing with the signal threshold, the sensor signal can be regarded as a normal signal if the signal feature of the sensor signal is the same as the signal feature of the exception signal and the sensor signal can be regarded as a fall signal if the signal feature of the sensor signal is different from the signal feature of the exception signal.

Figure 3:
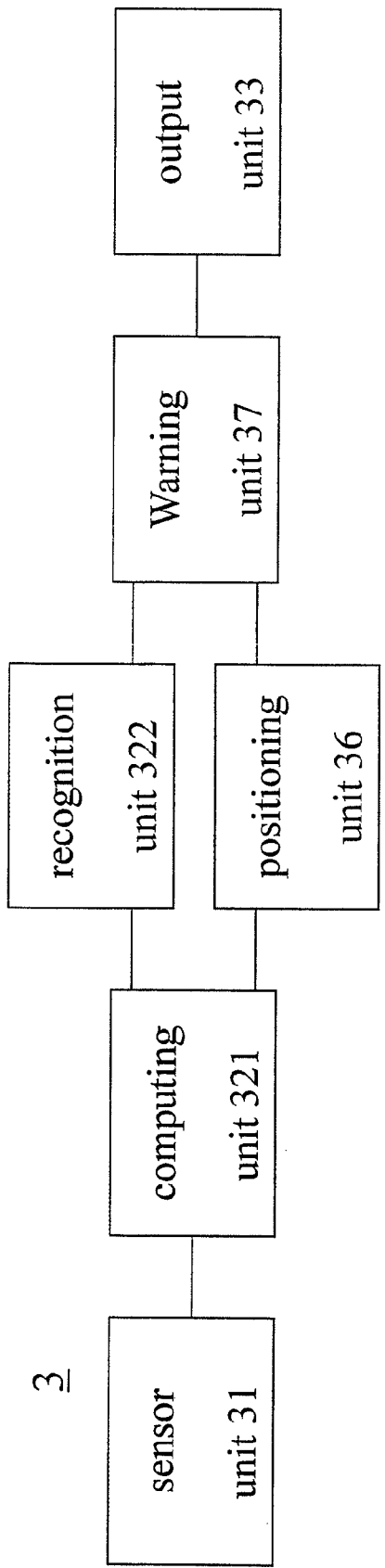
FIG. 3 is a block diagram illustrating the third embodiment of the fall positioning device 3 according to the present invention.

FIG. 3 is a block diagram illustrating the third embodiment of the fall positioning device 3 in the present invention. The fall positioning device 3 includes a sensor unit 31, a computing unit 321, a recognition unit 322, an output unit 33, a positioning unit 36 and a warning unit 37.

In the aforementioned embodiment, the sensor unit 31 can be a physiological sensor unit and/or the inertia sensor unit, wherein the physiological sensor unit can be an electromyography sensor unit and the inertia sensor unit can be an accelerometer and/or a gyroscope. The physiological signal measured by the physiological sensor unit can be computed by the computing unit 321 to estimate a distance having been moved and the moving direction of the user and the moving direction, such as going forwards, backwards, upwards or downwards or turning right or left.

In the aforementioned embodiment, the sensor signal measured by the sensor unit 31 can be computed by the computing unit 321 to obtain a computed result, wherein the computed result would be provided to the recognition unit 322 to determine whether the sensor signal is higher than a signal threshold or not. The recognition unit 322 would determine that the fall is going to happen if the sensor signal is higher than the signal threshold.

In general, the positioning device can not accurately obtain the location of the user in the interior space. Thus, in the aforementioned embodiment, the distance having been moved and the moving direction of the user computed by the computing unit 321 can be provided to the positioning unit 36 for obtaining the location of the user in the interior space.

Preferably, the positioning unit 36 obtains the location of the user via processing an arrangement of the interior space and the distance having been moved and the moving direction of the user in the interior space, wherein the arrangement is a compartment configuration and furnishings of the interior space. For example, the location of the user, such as sleeping in the bedroom, sitting on the couch or standing in front of the refrigerator, can be determined by processing the moving distance and the moving direction of the user and the arrangement of the house if the user is at home.

Preferably, the arrangement of the inertia space can be pre-stored in the positioning unit 36 or a memory unit to provide the positioning unit 36. In addition, the positioning unit 36 can be combined with the computing unit 321 so the computing unit 321 can directly process the arrangement and the distance and the moving direction to obtain the location of the user after computing the distance and the moving direction.

When the fall happens, the user would get injured by the fall. However, there might be some additional injuries corresponding to the location of the user. Thus, the additional injuries can be a predictable injury predicted by the fall recognition device 3 if the fall recognition device 3 can determine the location of the user accurately. For example, the user might get scalded or burned if the user falls in the kitchen.

In the aforementioned embodiment, when the recognition unit 322 determine the fall happens, the information, such as the predictable injury, can be determined by the warning unit 37 based on the location of the user. Therefore, the output unit 33 can transmits the information to an institution, such as a medical institution, a residential care home, etc. The medical workers in the institution can understand the health state of the user in advance and obtain a medical suggestion corresponding to the predictable injury of the user. Thus, the medical workers can design a medical plan for the user in advance before the medical worker reaches the location of the user.

Based on the above descriptions, it would be understood in the present invention that at least one of the first embodiment, the second embodiment and the third embodiment can be combined to determine whether the fall is going to happen, to obtain the location of the user, to provide the information, like the predictable injury and/or to take the exception signal into consideration.

While the invention has been described in terms of what are presently considered to be the most practical and preferred embodiments, it is to be understood that the invention should not be limited to the disclosed embodiment. On the contrary, it is intended to cover numerous modifications and variations included within the spirit and scope of the appended claims which are to be accorded with the broadest interpretation so as to encompass all such modifications and variations. Therefore, the above description and illustration should not be taken as limiting the scope of the present invention which is defined by the appended claims.

What is claimed is:

1. A fall positioning device, comprising:
    a sensor unit obtaining a sensor signal;
    a recognition unit processing the sensor signal to determine whether a fall is going to happen;
    a positioning unit obtaining a location of a controlled user in a space via processing an arrangement of the space and a distance having been moved and a moving direction of the controlled user in the space;
    a computing unit computing the sensor signal to obtain the distance having been moved and the moving direction and provide a computed result to the recognition unit for determining whether the fall is going to happen;
    a warning unit providing an information corresponding to the fall of the controlled user in the space; and
    an output unit transmitting the information to an institution to render a medical suggestion.

2. The fall positioning device as claimed in claim 1, wherein the information comprises a predicted injury corresponding to the location when the fall happens, and the arrangement is a compartment configuration and furnishings of an interior space.

3. The fall positioning device as claimed in claim 2, wherein the sensor unit is a physiological sensor unit.

* * * * *